(12) United States Patent
Segman

(10) Patent No.: US 10,441,203 B2
(45) Date of Patent: Oct. 15, 2019

(54) BIOPARAMETER DETERMINING DEVICE WITH SPACE-SAVING COMPONENT FOR APPENDAGE

(71) Applicant: Cnoga Medical Ltd., Caesarea (IL)

(72) Inventor: Yosef Segman, Zichron Yaacov (IL)

(73) Assignee: CNOGA MEDICAL LTD., Caesarea (IL)

( * ) Notice: Subject to any disclaimer, the term of this patent is extended or adjusted under 35 U.S.C. 154(b) by 206 days.

(21) Appl. No.: 15/706,792

(22) Filed: Sep. 18, 2017

(65) Prior Publication Data

US 2019/0083009 A1    Mar. 21, 2019

(51) Int. Cl.
  *A61B 5/1455* (2006.01)
  *A61B 5/145* (2006.01)
  *A61B 5/00* (2006.01)

(52) U.S. Cl.
  CPC ........ *A61B 5/1455* (2013.01); *A61B 5/14532* (2013.01); *A61B 5/14552* (2013.01); *A61B 5/6826* (2013.01); *A61B 2560/0431* (2013.01); *A61B 2562/0233* (2013.01); *A61B 2562/16* (2013.01); *A61B 2576/00* (2013.01)

(58) Field of Classification Search
  CPC .............. A61B 5/1455; A61B 5/14532; A61B 5/14552; A61B 5/6826
  USPC ....................................................... 600/334
  See application file for complete search history.

(56) References Cited

U.S. PATENT DOCUMENTS

| | | | |
|---|---|---|---|
| 4,825,879 A | 5/1989 | Tan et al. | |
| 5,891,021 A | 4/1999 | Dillon et al. | |
| 2006/0173247 A1 | 8/2006 | Medina | |
| 2008/0208023 A1 | 8/2008 | Gruvac | |
| 2008/0249393 A1 | 10/2008 | Finarov et al. | |
| 2010/0105996 A1* | 4/2010 | Segman | A61B 5/0205 600/322 |
| 2012/0191001 A1* | 7/2012 | Segman | A61B 5/14532 600/547 |
| 2014/0018647 A1* | 1/2014 | Segman | A61B 5/6826 600/322 |

* cited by examiner

*Primary Examiner* — Daniel L Cerioni
(74) *Attorney, Agent, or Firm* — Mark M. Friedman

(57) ABSTRACT

A space-saving structural component for a device, the device configured to non-invasively determine a tissue bioparameter of a mammalian subject, the component comprising a wall surface including a grooved recess and at least one shoulder; and a substantially flat cover, the cover configured to cover the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially flat state when the appendage is absent from the grooved recess, wherein in the closed position, when the appendage is absent from the recess, the cover is adjacent the at least one shoulder.

15 Claims, 4 Drawing Sheets

BIOPARAMETER DETERMINING DEVICE WITH SPACE-SAVING COMPONENT FOR APPENDAGE

FIELD AND BACKGROUND OF THE INVENTION

The present invention relates to non-invasive apparatuses for determining a bioparameter and having a space-saving component for receipt of an appendage of a person.

Portable devices for receipt of an appendage in a bioparameter determining device have a chamber for the appendage. Such devices are bulky.

SUMMARY OF THE INVENTION

One aspect of the invention is a space-saving structural component for a device, the device configured to non-invasively determine a tissue bioparameter of a mammalian subject, the component comprising a wall surface including a grooved recess and at least one shoulder; and a substantially flat cover, the cover configured to cover the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially flat state when the appendage is absent from the grooved recess, wherein in the closed position, when the appendage is absent from the recess, the cover is adjacent the at least one shoulder.

Another aspect of the invention is a portable device configured to non-invasively determine a tissue bioparameter of a mammalian subject, comprising a light source providing light within the device; a digital sensor; a processing unit; a space-saving component comprising: a wall surface including a grooved recess and at least one shoulder; and a substantially flat cover, the cover configured to cover the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially flat state when the appendage is absent from the grooved recess, wherein in the closed position, when the appendage is absent from the recess, the cover is adjacent the at least one shoulder, the chamber configured to receive the appendage such that the appendage is deployed adjacent the digital sensor and faces the light source.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a space-saving bioparameter determining device (for example a non-invasive glucose monitoring device that processes a picture of a finger inserted into a chamber therein) that when closed and when the appendage is not inserted in the device occupies a compact volume. Only when the appendage is inserted in the device, or if the cover of the device is opened, does the chamber defined by the cover and wall surface expand. A flexible portion of the cover is configured to deform elastically away from the wall surface upon insertion of an appendage, such as a finger. The cover is generally flat when the appendage is not inserted into the chamber of the device. This way, storage space is not utilized until the actual short interval during which the appendage is inserted. The wall surface may have a grooved recess and at least one shoulder.

The cover covers the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially flat state when the appendage is absent from the grooved recess, wherein in the closed position, when the appendage is absent from the recess, the cover is adjacent the at least one shoulder.

Accordingly, the cover is configured to cover the chamber, when the appendage is inserted in the chamber, such that light from the light source within the device is isolated from light outside the device, such as ambient light in the room in which the device is located. This optimizes the performance of the device, for example by maximizing the signal to noise ratio that the processor receives from the digital sensor.

The principles and operation of a Bioparameter Determining Device With Space-Saving Component for Appendage may be better understood with reference to the drawings and the accompanying description.

Figure 1:
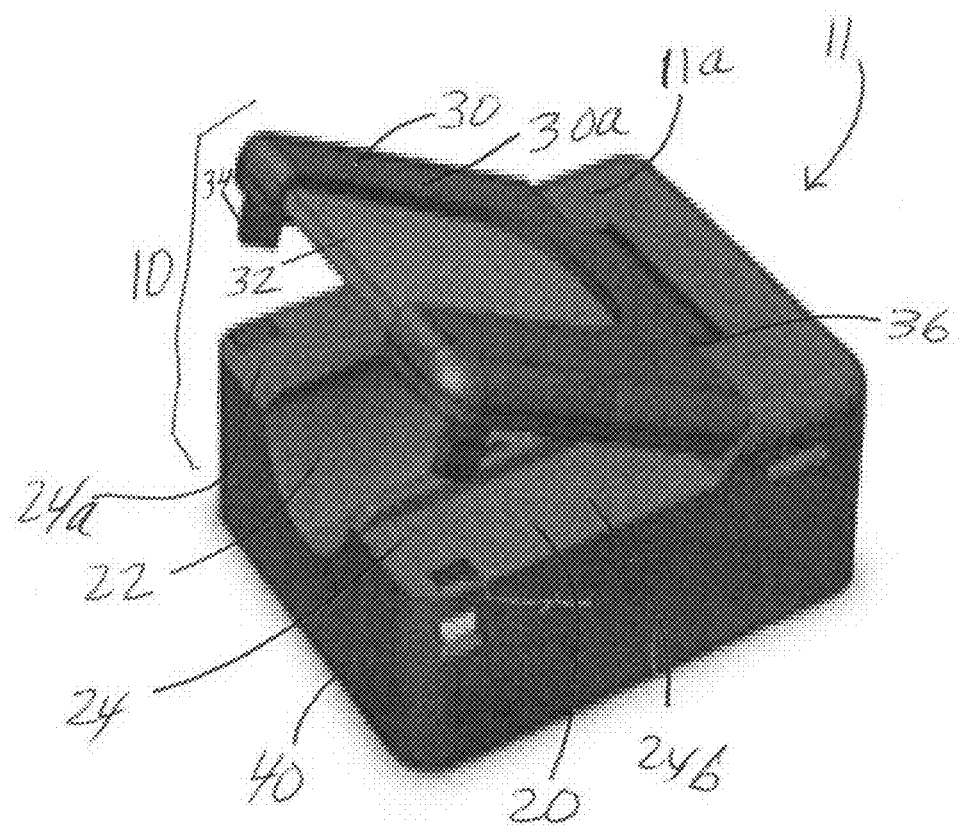
FIG. 1 is a photograph of a device shown from the front and side, in accordance with e embodiment of the invention.

As shown in FIG. 1, a device 11 configured to non-invasively determine a tissue bioparameter (for example glucose) of a mammalian subject has a space-saving structural component 10. Component 10, in one embodiment, comprises a wail surface 20 including a grooved recess 22 and at least one shoulder 24. Component 10 also comprises a cover 30 that may be substantially flat 8. Grooved recess 22, viewed from side to side when facing the device 11 from the front as shown in FIG. 2A, for example, is at least one of (i) substantially semi-arcuate and substantially U-shaped.

In one non-limiting example, the depth of the grooved recess is sufficient to accommodate a thickness of an average human finger. Many other variations of the depth are possible in accordance with the invention.

In certain embodiments, cover 30 is configured to cover wall surface 20 by moving from an open position far enough away from the wall surface 20 to allow insertion of an appendage 15 (FIG. 2A), for example a finger, of the subject into a chamber defined by the grooved recess 22 and the cover 30, to a closed position. The expanded state of chamber 28, due to the presence of appendage 15 and the nature of cover 30, is seen in FIG. 2A.

Figure 2A:
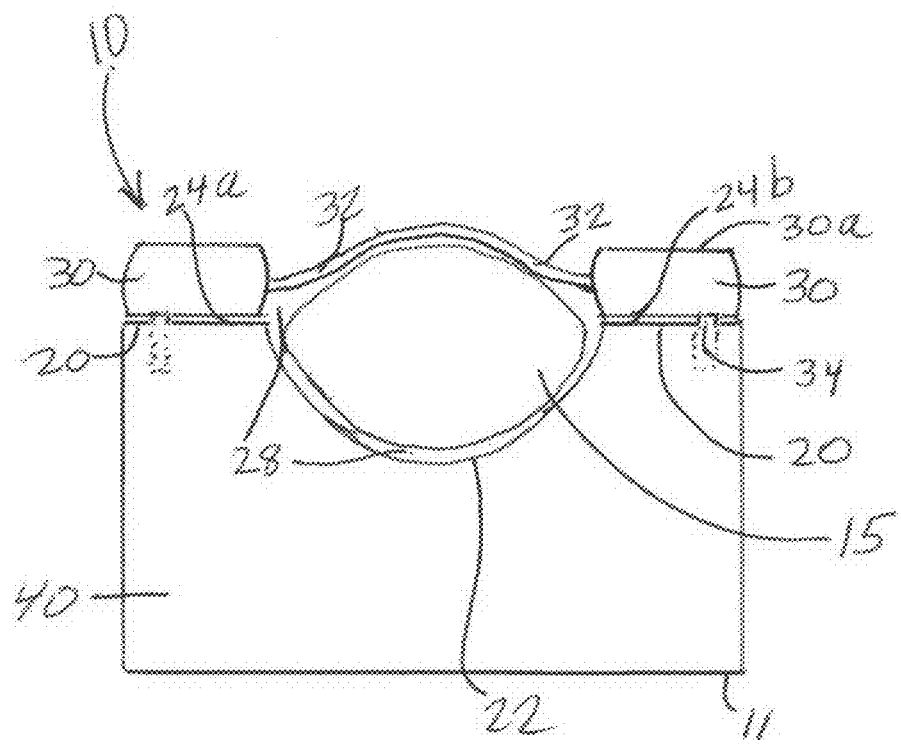
FIG. 2A is a schematic illustration of a front view of the device 11, including a component 10 having a chamber 28 for an appendage, and including the appendage, in accordance with one embodiment of the invention.
Figure 2B:
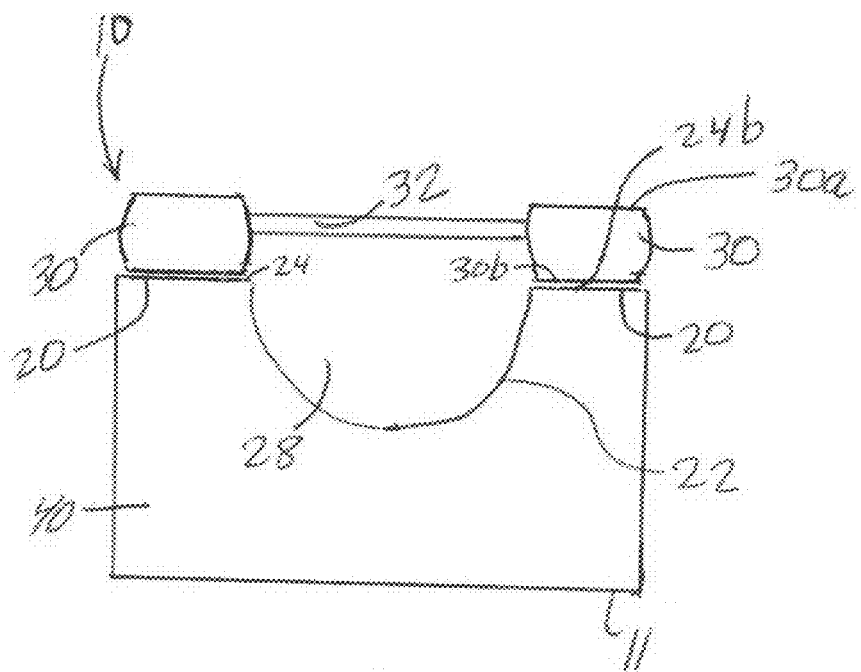
FIG. 2B is a schematic illustration of a front view of the device 11, including a component 10 having a chamber 28 for an appendage, but without the appendage, in accordance with one embodiment of the invention.

As shown further in the particular embodiment depicted in FIG. 1 and in FIGS. 2A-2B, cover 30 also comprises a flexible material 32. In the closed position, when appendage 15 is absent from the recess, as shown in FIG. 2B and when appendage 15 is present as shown in FIG. 2A, flexible material 32 covers the groove. Flexible material 32 is elastic. In some embodiments, flexible material 32 is one of, or a combination of, rubber, foam and silicon.

Flexible material 32, in the closed position, may elastically deform away from the wall surface 20 when the appendage 15 is present in the grooved recess 22 (FIG. 2A) and may restore to a substantially flat state when the appendage 15 is absent from the grooved recess 22 (FIG. 2B). Furthermore, in the closed position shown in FIG. 2B, when the appendage 15 is absent from the recess 22, cover 20 may be adjacent the at least one shoulder 24.

Figure 3:
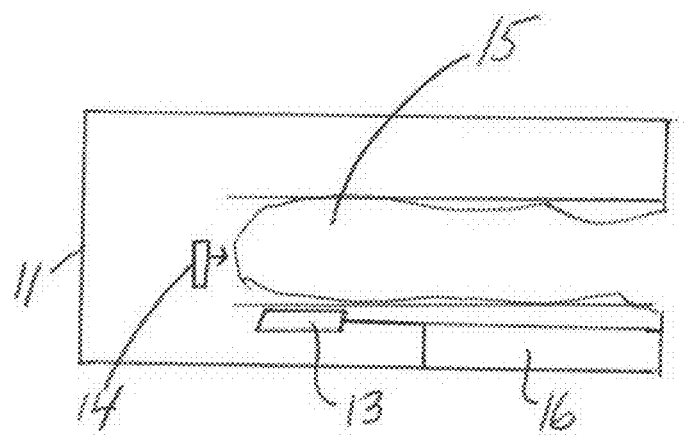
FIG. 3 is a schematic view from the side of a device 11 that shows an appendage configured to face a light source and to cover a digital sensor within the device, in accordance with one embodiment of the invention.

As seen from FIG. 3, device 11 in some embodiments has a digital sensor 13 and a light source 14. Light from the light source impacts the appendage 15, traverses the tissue in the appendage, and then impacts the digital sensor 13 to produce an image. A processing unit 16 receives a signal (for example corresponding to spatial-temporal color pixel information of the image) from the digital sensor 13 and processes it, yielding a bioparameter value, which may be displayed on a display (not shown). Accordingly, the chamber 28 is configured to receive the appendage 15 such that appendage 15 is deployed adjacent the digital sensor and faces the light source, for example axially, as shown schematically in FIG. 3 (with the arrow showing direction of light from light source 14 impacting tip of a finger 15 axially).

In the closed position, as shown schematically in FIG. 2A and FIG. 2B, cover 30 contacts the at least one shoulder 24 (in other embodiments cover 30 stops just short of contact, as controlled by hinge 36). Accordingly, cover 30 is configured to cover chamber 28, when appendage 15 is present in chamber 28 on the grooved recess 22 and cover 30 is closed, such that light within the device 11 (for example from light source 14), and most particularly light within chamber 28, is sealed off from, or at least substantially sealed off or isolated from, light outside device 11, for example from ambient light in the room in which the device 11 is located.

In the simplest embodiment shown in FIG. 1, grooved recess 22 is in a central portion of wall surface 20. Accordingly, the at least one shoulder 24 comprises two shoulders 24a, 24b of relatively equal width. In this case, moreover, flexible material 32 is in a central area, or is in at least a central area, of cover 30 (along the dimension moving from one side of device 11 to the other side) because recess 22 is in a central portion of wall surface 20. In other embodiments, recess 22 is less centrally located, or located from a side edge of wall surface 20, in which case the at least one shoulder 24 is only one shoulder 24 in some embodiments. Furthermore, although the at least one shoulder 24 is shown in the figures as flat or at least substantially flat or substantially planar, certain other embodiments could utilize at least one shoulder that is not flat, such as curved. In that case, it would be expected that a lower surface of cover 30 would at least generally conform to the contour of at least one shoulder 24, and be similarly curved, to create the sealing or substantial isolation of chamber 28 mentioned above from light outside the device 11.

In one non-limiting example, as shown in FIG. 1, in the closed position, an outer surface 30a of the cover 30 is substantially level with a remaining outer surface 11a of the device 11 to form together a facade of the device 11. Although this is not a requirement, it serves to further save space.

Cover 30 may swing for example on a hinge 36 whose range of motion is from zero to as much as 180 degrees in some options. In some embodiments, cover 30 is at least one of: (i) hinged and (ii) flexes on an axis distal to an initial point of insertion of appendage 15. For reference, the initial point of insertion of appendage 15 is in the front of the device 11 where the appendage passes front wall 40 (FIG. 1).

In fact, in some embodiments, in the closed position, in the absence of the appendage, the cover 30 locks into the wall surface 20 for example by means of prongs 34. As shown in FIG. 2A in dotted lines, prongs 34 penetrate shoulders 24a, 24b of component 10 of device 11 and lock cover in place to ensure that the space-saving compactness of component 10 and device 11 is not lost by accidental opening of cover 30. In some embodiments, in the closed position, in the absence of the appendage 15, a bottom surface 30h (see FIG. 2B) of cover 30 touches wall surface 20 (irrespective of the existence of any prongs 34).

One embodiment of the invention is a portable device configured to non-invasively determine a tissue bioparameter of a mammalian subject, comprising: a light source; a digital sensor; a processing unit and a space-saving component.

Any or all of the structural features of the space-saving component 10 described above apply as well to this embodiment defined to be the device 11 that includes the space-saving component 10. For example, the space-saving component may comprise a wall surface including a grooved recess and at least one shoulder; and a substantially flat cover, the cover configured to cover the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially flat state when the appendage is absent from the grooved recess, wherein in the closed position, when the appendage is absent from the recess, the cover is adjacent the at least one shoulder, the chamber configured to receive the appendage such that the appendage is deployed adjacent the digital sensor and faces the light source.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A space-saving structural component for a device, the device configured to non-invasively determine a tissue bioparameter of a mammalian subject, the component comprising:
   a wall surface including a grooved recess and at least one shoulder; and
   a substantially flat cover,
   the cover configured to cover the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially fiat state when the appendage is absent from the grooved recess, wherein in the closed position, when the appendage is absent from the recess, the cover is adjacent the at least one shoulder.

2. The device of claim 1, wherein the device has a digital sensor and a light source and wherein the chamber is configured to receive the appendage such that the appendage is deployed adjacent the digital sensor and faces the light source.

3. The device of claim I, wherein, in the closed position, an outer surface of the cover is level with a remaining outer surface of the device to form together a facade of the device.

4. The device of claim 1, wherein the flexible material spans at least a central area of the cover.

5. The device of claim 1, wherein the cover is at least one of: (i) hinged and (ii) flexes on an axis distal to an initial point of insertion of the appendage.

6. The device of claim 1 wherein, in the closed position, when the appendage is absent from the recess, the flexible material covers the groove.

7. The device of claim 1, wherein the grooved recess, going from side to side when facing the device, is at least one of (i) substantially semi-arcuate and substantially U-shaped.

8. The device of claim 1, wherein the at least one shoulder is substantially planar.

9. The device of claim 1, wherein the flexible material is elastic.

10. The device of claim 1, wherein the flexible material is one of, or a combination of, rubber, foam and silicon.

11. The device of claim 1, wherein the cover is configured to cover the chamber in a closed position of the cover, when the appendage is inserted in the chamber, such that light within the device is substantially isolated from light outside the device.

12. The device of claim 1, wherein in the closed position, in the absence of the appendage, the cover locks into the wall surface.

13. The device of claim 1, wherein in the closed position the cover contacts the at least one shoulder.

14. A portable device configured to non-invasively determine a tissue bioparameter of a mammalian subject, comprising:
   a light source providing light within the device;
   a digital sensor;
   a processing unit;
   a space-saving component comprising:
   (a) a wall surface including a grooved recess and at least one shoulder; and
   (b) a substantially flat cover,
   the cover configured to cover the wall surface by moving from an open position far enough away from the wall surface to allow insertion of an appendage of the subject into a chamber defined by the grooved recess and the cover, to a closed position, the cover comprising a flexible material that, in the closed position, elastically deforms away from the wall surface when the appendage is present in the grooved recess and restores to a substantially flat state when the appendage is absent from the grooved recess, wherein in the closed position, when the appendage is absent from the recess, the cover is adjacent the at least one shoulder,
   the chamber configured to receive the appendage such that the appendage is deployed adjacent the digital sensor and faces the light source.

15. The device of claim 14, wherein the cover is configured to cover the chamber, when the appendage is inserted in the chamber and the cover is closed, such that light within the device is substantially isolated from light outside the device.

* * * * *